United States Patent [19]

Rohde et al.

[11] Patent Number: 4,557,147
[45] Date of Patent: Dec. 10, 1985

[54] BORE HOLE ROCK SHEAR TESTER AND METHOD FOR USING SAME

[75] Inventors: John R. Rohde, Ames; John M. Pitt, Nevada, both of Iowa

[73] Assignee: Iowa State University Research Foundation, Inc., Ames, Iowa

[21] Appl. No.: 609,967

[22] Filed: May 14, 1984

[51] Int. Cl.$^4$ .......................... G01N 3/24; G01N 33/24
[52] U.S. Cl. ........................................... 73/784; 73/84; 73/845
[58] Field of Search ................... 73/151, 784, 84, 845, 73/841

[56] References Cited

U.S. PATENT DOCUMENTS

| | | | |
|---|---|---|---|
| 3,349,610 | 10/1967 | Noel | 73/84 |
| 3,427,871 | 2/1969 | Handy | 73/84 |
| 3,610,035 | 10/1971 | Handy | 73/784 |
| 3,673,861 | 7/1972 | Handy | 73/84 |
| 4,030,345 | 6/1977 | Edmond | |
| 4,075,885 | 2/1978 | Handy | 73/845 |

FOREIGN PATENT DOCUMENTS 1007263 10/1965 United Kingdom ................... 73/84

*Primary Examiner*—Howard A. Birmiel
*Attorney, Agent, or Firm*—Zarley, McKee, Thomte, Voorhees & Sease

[57] ABSTRACT

The bore hole rock shear testing device of the present invention comprises a case assembly having a longitudinal axis, a driving block, at least one wedge member, and a restraint member. The wedge member is positioned between the restraint member and the driving block and includes a rock engaging surface facing radially outwardly from the longitudinal axis of the case assembly. The driving block and the wedge member have complimentary tapered surfaces which cause the rock engaging surface to be urged radially outwardly when the wedge member is compressed or squeezed between the driving block and the restraint member. Power means are provided for moving the driving block toward the restraint member, and a restraint mechanism selectively holds the restraint member against movment. The restraint mechanism is movable to an inoperative position which results in both outward radial forces and axial forces being applied simultaneously to the rock engaging surface when the driving block is moved toward the wedge member and the restraint member.

12 Claims, 5 Drawing Figures

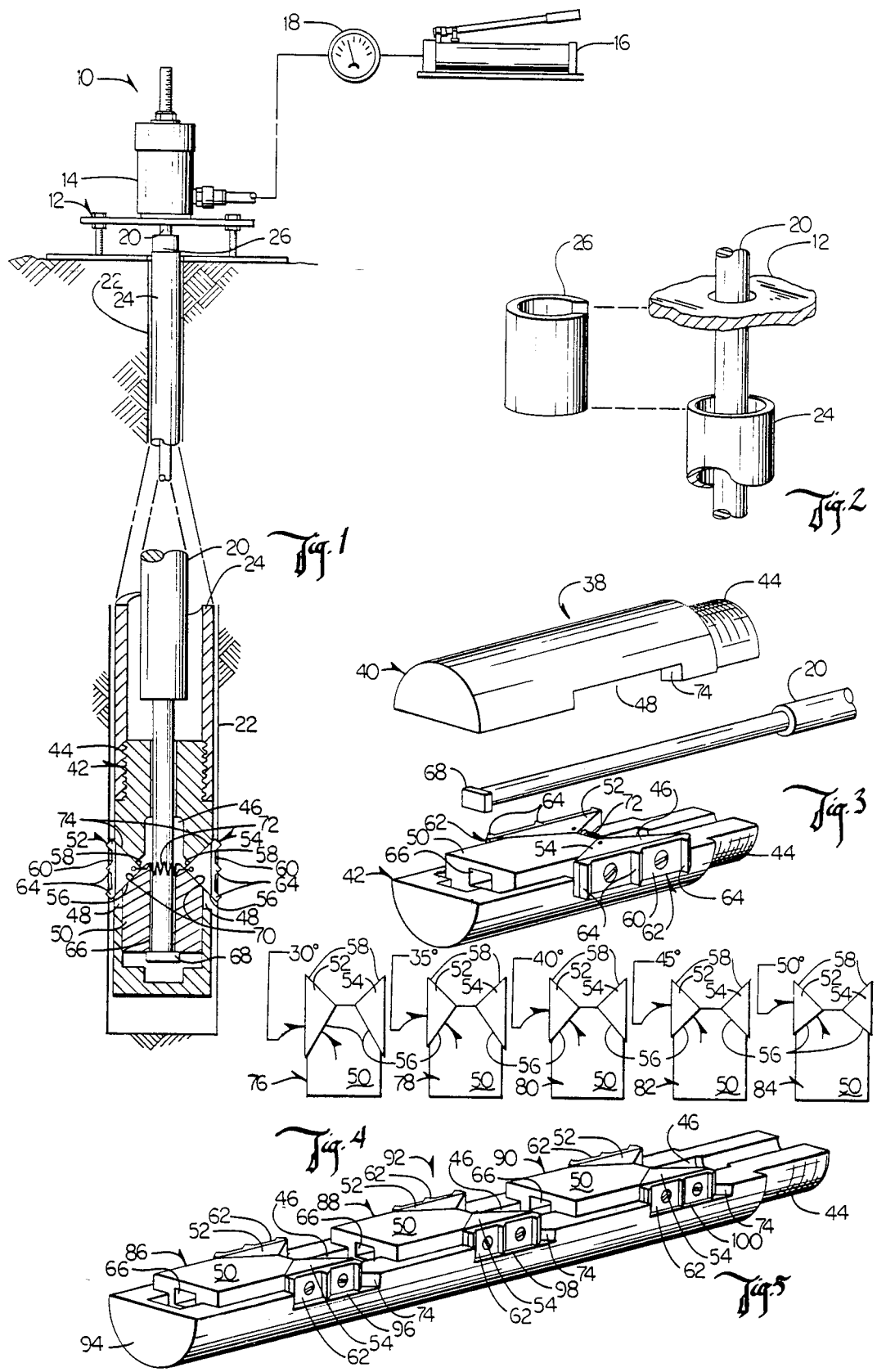

BORE HOLE ROCK SHEAR TESTER AND METHOD FOR USING SAME

GRANT REFERENCE

This invention is based upon work supported by the Bureau of Mines, Department of Interior, United States Government, under Grant No. G1106002.

BACKGROUND OF THE INVENTION

This invention relates to a bore hole rock shear tester and method for using same.

In many mining and excavating operations, it is desirable to test the shear strength of rock being excavated or mined. Sometimes this is done by taking samples of the rock to the laboratory. However, such laboratory tests are often costly and biased. A more cost effective and unbiased manner of testing is to bore a hole in the rock in its natural environment.

In situ shear strength testing of the rock is accomplished by boring a hole and by inserting test equipment into the hole. The test equipment is used to engage an envelope of material on the wall of the bore hole. Then, radial and axial forces are exerted on the envelope of material until shearing occurs.

Previous devices for accomplishing this rock bore hole shear test are cumbersome and difficult to use. These devices require a large diameter test bore hole. This required large diameter of the test bore hole causes the tests in rock to be very expensive. If it were possible to use a smaller diameter bore hole, these tests would be easier to conduct and less expensive.

Previous bore hole testing devices required independent apparatus for exerting normal and axial forces on the walls of the bore hole. The equipment for normal stress application included hydraulic cylinders which were embodied in the device and which were inserted into the hole with the device. Because this equipment was required to be inserted into the bore hole, there was a necessity for a rather large diameter bore hole in order to conduct the test.

Prior devices for conducting the rock bore hole shear test were cumbersome to use. It was necessary to remove these devices from the hole several times during the test so that they could be cleaned and checked to assure proper readings.

Therefore, a primary object of the present invention is an improved rock bore hole shear testing device and method for using same.

A further object of the present invention is the provision of a testing device which permits the application of normal and axial forces to the wall of the bore hole with apparatus which is located externally of the bore hole.

A further object of the present invention is the provision of a device which could operate within a hole which is one and one-half inches in diameter, the diameter commonly used in mining, for roof bolting and blasting.

A further object of the present invention is the provision of a device and method for using same, which would require only one insertion of the testing device into the bore hole.

A further object of the present invention is the provision of a device which can be applicable to both shallow and deep testing holes.

A further object of the present invention is the provision of a device which is simple in construction and operation so that it can be used by a mining crew involved in regular drilling processes.

A further object of the present invention is the provision of a device which permits first, the application of a normal force to seat the testing apparatus firmly in the walls of the bore hole, and second, to permit the simultaneous application of both a normal and an axial force to the bore hole wall so as to determine the point at which the device causes shearing in the walls of the bore hole.

A further object of the present invention is the provision of a device which is economical to manufacture, durable in use and efficient in operation.

SUMMARY OF THE INVENTION

The present invention utilizes a system of wedges for exerting first a normal force to rock bore hole wall, and then for applying both an axial and an outward radial force with wedges until the shearing occurs in the walls of the rock bore hole. The device permits the application of these forces by means of apparatus which is located externally of the holes.

The device includes an elongated rod which extends from above the ground down into the hole. Carried by the lower end of the rod is a drive block which includes tapered surfaces for engaging a pair of wedge blocks located immediately thereabove. The wedge blocks have tapered surfaces which bear against the tapered surfaces of the drive block. Bearings or other friction reducing media may be used at those interfaces so as to reduce friction. When the rod is pulled vertically upwardly, the cooperating tapered surfaces of the wedge blocks and the drive block cause the wedge blocks to be forced radially outwardly, and also cause the exertion of an upward axial force to the wedge blocks.

A restraint member is positioned above the wedge blocks and is adapted to be moved from an operative position wherein it restrains the wedge blocks from axial upward movement to an inoperative position wherein it permits the wedge blocks to move axially upwardly. When the restraint mechanism is in its operative position, and when the rod is pulled vertically upwardly, the restraint member neutralizes the upward axial forces on the wedge blocks, thereby permitting the application of only an outward radial force on the wedge blocks. This causes the wedge blocks, which have teeth on their outwardly facing surfaces, to engage the walls of the rock bore hole and to embed the teeth in the walls of the rock bore hole.

After the teeth are embedded in the walls of the bore hole, the restraint member is moved to its inoperative position. Then an upward pulling force is again exerted on the rod so as to cause the drive block to exert both an upward axial force and an outward radial force to the wedge blocks. These forces are increased gradually until the wedge blocks cause shearing in the walls of the rock bore hole. At the time that shearing occurs, the forces being exerted on the wedge block are measured and recorded.

The wedge blocks and driving block are removable from the device so that different wedge blocks and driving blocks can be inserted. Different sets of wedge blocks and driving blocks are used, each having complementary tapered surfaces which extend at different angles. By substituting different sets and by repeating the process described above, it is possible to obtain a plurality of readings for wedge members having different angles.

By changing the tapered angles of the wedge blocks from one test to another, it is possible to vary the relative magnitudes of the radial and axial forces applied to the wedge blocks. This permits the taking of a number of different readings, wherein the axial and radial forces applied to the wedge blocks are varied.

In a modified form of the invention, a plurality of sets of wedge blocks and driving blocks are mounted within a housing, and each of them may be operated independently for separate tests and readings without the need for removing the device from the bore hole to replace the sets of blocks and wedge members.

BRIEF DESCRIPTION OF THE FIGURES OF THE DRAWINGS

FIG. 1 is a sectional view showing the device mounted within a bore hole, with the lower end of the bore hole being shown in enlarged view.

FIG. 2 is a perspective view of the lock which is utilized in connection with the restraint mechanism.

FIG. 3 is an exploded perspective view of the lower end of the present invention.

FIG. 4 is a view showing five separate sets of wedge blocks and drive blocks which can be used in the present invention.

FIG. 5 is a perspective view of a modified form of the present invention.

DETAILED DESCRIPTION OF THE PREFERRED EMBODIMENT

Referring to the drawings, the numeral 10 generally designates the device of the present invention. Device 10 includes a platform frame 12 which supports a hydraulic cylinder 14, which is operatively connected to a hand hydraulic pump 6. A pressure gauge 18 is included within the hydraulic circuitry to register the hydraulic pressure therein.

Connected to the hollow piston rod of the hydraulic cylinder 14 is a draw rod 20 which extends downwardly into a cylindrical rock bore hole 22. Surrounding draw rod 20 is a restraint pipe 24 which also extends downwardly into rock bore hole 22. Restraint pipe 24 is free to slide vertically with respect to draw rod 20. A cylindrical lock spacer 26 may be used to lock restraint pipe 24 against vertical movement. Spacer 26 includes a vertical slot therein which permits spacer 26 to be inserted or removed from the space between the upper end of restraint pipe 24 and the platform frame 12. FIG. 1 shows the spacer 26 inserted, and FIG. 2 shows it removed.

The lower end of restraint pipe 24 is secured to a wedge retaining case formed by body member 38. Body member 38 is comprised of two body member halves 40, 42 which are held together whenever restraint pipe 24 is attached over the threaded neck 44 which is formed at one end of body halves 40, 42.

The two body halves 40, 42 combine to form body member 38 which has a cavity 46 formed therein. Cavity 46 includes a pair of oppositely positioned rectangular windows 48 formed in opposite sides thereof, and providing communication from outside body member 38 to the interior of cavity 46.

Positioned within cavity 46 are a drive block 50 and a pair of wedge members 52, 54. Wedge members 52, 54 are identical in construction and each include tapered surfaces, which for purpose of reference, will be identified as a downwardly presented tapered surface 56, and an upwardly presented tapered surface 58. Wedge members 52, 54 also each include surface 60 presented radially outwardly with respect to the longitudinal axis of bore hole 22. Surface 60 is formed by a shear plate 62. Shear plate 62 includes several wedge shaped teeth 64 for engaging the walls of the rock bore hole 22. Wedge members 52, 54 are positioned within windows 48 and are radially movable inwardly and outwardly with respect to the longitudinal axis of the rock bore hole 22.

Drive block 50 includes a rectangular hole 66 extending vertically therethrough. Extending through this hole 66 is the lower end of rod 20. On the extreme lower end of rod 20 is a rectangular block 68 which is sized to fit within the rectangular hole 66 so that it can be extended therethrough. However, because of the rectangular shape of block 68 and hole 66, it is possible to rotate rod 20 90° after extending block 68 through hole 66. This 90° rotation prevents block 68 from sliding back out of opening 66. Thus, as shown in FIG. 1, it is possible to pull upwardly on rod 22 and thereby exert an upward force on drive block 50.

The upper end of drive block 50 is provided with a pair of upwardly presented angular or tapered surfaces 70 which are complementary to and which engage the downwardly presented tapered surfaces 56 of wedge members 52, 54. The tapered surfaces 56 of wedge members 52, 54 and the tapered surfaces 70 of drive block 50 cooperate during upward movement of rod 22 to exert both an outward radial force and an upward axial force on the wedge members 52, 54. Wedge members 52, 54 are yieldably urged radially inwardly by means of a spring 72.

Each body member half 40, 42 is provided with a downwardly angled tapered surface 74 which is complementary to and which engages one of the upwardly presented tapered surfaces 58 of wedge members 52, 54. Because body member 38 is threadably secured to restraint pipe 54, it is possible to prevent upward axial movement of wedge members 52, 54 merely by inserting lock spacer 26 between the upper end of pipe 24 and frame 12 as is shown in FIG. 1. When lock spacer 26 is inserted in this manner, and when rod 20 is pulled upwardly, the downwardly presented tapered surfaces 74 of body halves 40, 42 restrain upward movement of wedge members 52, 54, and also contribute to and facilitate the exertion of a radial outward force on wedge members 52, 54.

The rock bore hole test is accomplished in the following manner. Initially a test bore hole 22 is drilled. With the present invention, it is possible to drill a hole having a smaller diameter than previously required. It can be made an inch and a half in diameter or smaller if desired.

After the bore hole has been drilled, the platform frame 12 is placed in position as shown in FIG. 1. Body member 38 is assembled with drive block 50 and wedge members 52, 54 within cavity 46. Rod 20 is inserted through pipe 24 and through the rectangular opening in drive block 50 and rotated 90° so as to attach rod 20 to drive block 50. Restraining pipe 24 is then threaded over the threaded neck 44 of body member 38. Rod 20 and pipe 24 can be constructed in segments which may be threaded or coupled together to accommodate holes of different depths.

After assembly, body member 38 is inserted into the test bore hole to the desired depth. Rod 20 is coupled (not shown) to the piston rod of hydraulic cylinder 14, and lock spacer 26 is inserted to the position shown in FIG. 1 so as to hold restraining pipe 24 against upward movement.

Pump 16 is then manually manipulated so as to increase the pressure within cylinder 14. The hydraulic pressure is registered on gauge 18.

As the pressure within cylinder 14 increases, rod 20 is drawn vertically upward. This upward movement of rod 20 causes drive block 50 also to be urged upwardly so that the complementary tapered surfaces 56, 70 of wedge members 52, 54 and drive block 50, cooperate to urge the wedge blocks radially outwardly. Because lock spacer 26 is inserted, restraining pipe 22 holds body member 38 against vertical movement in response to the upward vertical movement of rod 20. This causes the downwardly presented tapered surfaces 74 of body member halves 40, 42 to engage the upwardly presented tapered surfaces 58 of wedge members 52, 54. The resulting reaction is that wedge members 52, 54 are squeezed between the two axial forces exerted by upwardly moving block 50 and the stationary body member halves 40 and 42. The result of this interaction is that wedge members 52, 54 are forced radially outwardly, and are held against upward axial movement within the test bore hole 22.

As the outward radial force on blocks 52, 54 is increased, the teeth 64 of shear plates 62 are embedded in the rock walls of bore test hole 22. After teeth 62 are embedded, the pressure within hydraulic cylinder 14 is reduced.

The next step in the testing process is to remove lock spacer 26 so that restraining pipe 24 and body member 38 are free to move upwardly in unison with the upward movement of rod 20. After lock spacer 26 is removed, pump 16 is again manually operated to cause the draw rod 20 to be urged upwardly. Because body member 38 and restraint pipe 24 are free to move upwardly also, there are two resulting forces exerted on the wedge blocks 52, 54. The tapered complementary surfaces 70, 56 of drive block 50 and wedge blocks 52, 54 cause the wedge blocks to be urged in a radial direction and also in an axial direction. The relationship between the axial force and the radial force is determined by the angle of the complementary tapered surfaces 70, 56.

By operating pump 16, it is possible to gradually increase the force with which rod 20 is pulled upwardly. As this force increases, the axial and radial forces exerted on wedge blocks 52, 54 are also increased. At some point, the teeth 64 which are embedded within the rock wall of bore test hole 22, will begin shearing an envelope of material on the rock wall of the test bore hole. At this point, the reading on meter 18 is taken so as to determine the forces necessary to cause shearing in the rock walls.

The relationship between the axial and radial forces exerted on the wedge members is determined by the angle of the complementary tapered surfaces 56, 70. In order to obtain different readings for analysis of the shear characteristics of the rock surrounding the test bore hole, it is possible to replace block 50 and wedge blocks 54 with a new assembly having complementary tapered surfaces 70, 56 which are different from the first wedge drive block assembly.

FIG. 4 illustrates five different wedge and drive block assemblies which may be utilized. The angles of complementary tapered surfaces 70, 56 are shown in FIG. 4 to be varied from 30° in assembly 76, to 35° in assembly 78, to 40° in assembly 80, to 45° in assembly 82, to 50° in assembly 84. Other assemblies having different angular tapered surfaces may also be utilized to obtain additional readings. Each assembly 76–84 can be inserted into the body member 38 and used for a test reading in accordance with the process described above. With each separate assembly, a different reading will be obtained at the point that shearing occurs. These various readings may be plotted and analyzed to determine the characteristics of the rock surrounding the test bore hole.

Referring to FIG. 5, a modified form of the invention is shown which permits the use of a plurality of drive block wedge block assemblies 86, 88, 90. The numeral 92 is used to generally designate this modified form of the invention. Device 92 includes two body member halves 94 which are similar to body member halves 40 and 42, but which includes three windows 96, 98, 100 for receiving the wedge members 52, 54 of assemblies 86, 88, 90, respectively. The remaining parts of the device are the same as shown in FIGS. 1–4, and corresponding numerals are used to indicate such parts. The wedge block members 52, 54 of each assembly 86, 88, 90 have a different angle of tapered surface, so that a plurality of readings can be obtained with the device 92.

Device 92 is utilized by inserting rod 20 through the square opening 66 of all three of the assemblies 86, 88, 90. Rod 20 is then rotated 90° so that the rectangular block 68 engages drive block 50 of assembly 86. The test is then conducted in the same fashion as described for the device shown in FIGS. 1–4, with the wedge members first being spread apart to embed the teeth 64 in the rock walls, and with the simultaneous application of axial and radial forces until shearing occurs. After a reading has been obtained by conducting a test with assembly 86, rod 20 is rotated 90° and the rod is withdrawn upwardly from assembly 86. Rod 20 is then rotated 90° so that the rectangular block 68 engages drive block 50 of assembly 88. A second test is then conducted, and different readings will be obtained by virtue of the different angles of the complementary tapered surfaces between drive block 50 and wedge blocks 52, 54.

After the second test has been completed, rod 20 is rotated 90° and withdrawn upwardly to engage block 50 of assembly 90. A third test can then be run, and a third set of readings attained for the particular angle utilized in assembly 92. Thus, with the device shown in FIG. 4, it is possible to obtain three separate readings without the need for removing the device from the hole.

The device of the present invention is a significant improvement over prior devices. It is simple and easy to operate. It requires a hole having a diameter of only one and one-half inches, and the hydraulic apparatus such as cylinder 14 and pump 16 can be kept outside the bore hole so as to permit a smaller bore hole to be used. The device provides a simple means for initially embedding the teeth 64 in the walls of the rock bore test hole. Prior devices were unable to accomplish this initial step of the procedure without cumbersome equipment which occupied significant space within the rock bore hole.

The present invention also permits the application of both an outward radial and an upward axial force in order to conduct the shear test. Furthermore, by utilizing wedges having different angled surfaces, it is possible to obtain a number of readings so as to provide a more thorough analysis of the shear characteristics of the rock surrounding the test bore hole.

In some applications, it may be desirable to conduct tests in deep bore holes. In these situations a modified form of the invention may be utilized wherein the hydraulic cylinders for operating the device are lowered down into the hole with the device. The cylinders can be used to force the driving block against the wedges so as to cause a resulting force against the bore hole wall in both an axial and radial direction with respect to the axis of the bore hole.

Thus, it can be seen that the device accomplishes at least all of its stated objectives.

What is claimed is:

1. A bore hole rock shear testing device for use in a bored rock hole having rock walls, said device comprising:
    a case assembly having a longitudinal axis and comprising a driving block, at least one wedge member, and a restraint member,
    said wedge member being positioned between said driving block and said restraint member, said wedge member having a rock engaging surface facing radially outwardly with respect to said longitudinal axis of said case assembly and said wedge member also having a first tapered wedge surface;
    said driving block having a tapered block surface which is complimentary to and which engages said first tapered wedge surface,
    power means for forcing said driving block in an axial direction towards said wedge member and said restraint member,
    restraint mechanism associated with said restraint member and being movable to an operative position for holding said restraint member against movement in response to movement of said driving block towards said wedge member and said restraint member, whereby said tapered block surface and said first tapered wedge surface cooperate to force said rock engaging surface of said wedge member radially outwardly with respect to said longitudinal axis of said case assembly;
    said restraint mechanism being selectively movable to an inoperative position whereby said restraint member is free to move axially in response to axial movement of said block toward said wedge member and said restraint member whereby said first tapered wedge surface and said tapered block surface will cooperate to exert a simultaneous axial and outward radial force on said rock engaging surface.

2. A device according to claim 1 wherein spring means yieldably urge said wedge member radially inwardly toward said longitudinal axis of said case assembly.

3. A device according to claim 1 wherein said restraint member includes a tapered restraint surface, said wedge member having a second tapered wedge surface complementary to and engaging said tapered restraint surface of said restraint member, whereby said tapered restraint surface and said second tapered wedge surface cooperate to facilitate radial outward movement of said wedge member in response to movement of said driving block toward said wedge member and said restraint member whenever said restraint mechanism is in said operative position.

4. A device according to claim 1 wherein said case assembly further comprises a second wedge member positioned between said driving block and said restraint member, said second wedge member having a rock engaging surface facing radially outwardly with respect to said longitudinal axis of said case assembly, and also having a first tapered wedge surface, said driving block having a second tapered block surface complementary to and engaging said second tapered wedge surface for camming said second wedge member radially outwardly from said longitudinal axis of said case assembly in response to movement of said driving block, toward said restraint member and said wedge member, said restraint member engaging both said first and second wedge members.

5. A device according to claim 4 wherein said rock engaging surfaces of said first and second wedge members each include teeth for frictionally engaging said rock walls within said test bore hole.

6. A device according to claim 1 wherein an elongated member includes a lower end operatively connected to said driving block and an upper end operatively connected to said power means for causing movement of said driving block toward said wedge member and said restraint member, in response to actuation of said power means.

7. A device according to claim 6 wherein said restraint member comprises an elongated pipe surrounding said elongated members and having a lower end connected to said case assembly.

8. A device according to claim 7 wherein said power means is operatively mounted to a frame adapted to be located outside said hole, said upper end of said elongated pipe being connected to said power means, said restraint mechanism comprising a lock spacer which is removably fitted between said restraint member and said frame to limit movement of said restraint member toward said frame.

9. A method for making a rock bore hole test in a rock bore hole having cylindrical rock walls, said method comprising:
    inserting a pair of wedge members into said hole, said wedge members each comprising a rock engaging surface facing radially outwardly from the vertical axis of said hole, each of said rock engaging surfaces including teeth for engaging said rock walls;
    spreading said wedge members radially outwardly in opposite directions until said teeth engage and partially embed themselves within said rock wall;
    simultaneously exerting an upward axial force and an outward radial force to said wedge members,
    increasing the magnitude of said axial and radial forces until the axial force causes said teeth of said wedge members to shear said rock walls of said bore hole;
    registering the magnitude of said axial and radial forces at the time of said shearing;
    said simultaneous exertion of said upward axial and outward radial forces being accomplished by pulling upwardly on a rod having a drive block attached thereto, said drive block having a tapered cam surface which engages a complimentary tapered surface on each of said wedge members, said tapered surfaces camming against one another during said upward pulling of said rod and causing both of said upward axial force and said outward radial force to be exerted on said wedge members.

10. A method according to claim 9 wherein said spreading of said wedge members is accomplished by restraining said wedge members against upward axial movement during upward pulling of said rod so as to neutralize the upward axial force exerted on said wedge members and thereby expose said wedge members to a resultant force extending only in said outward radial direction.

11. A method according to claim 9 and further comprising removing said wedge members and said drive block and replacing them with a new drive block and new wedge members, the tapered complementary surfaces of said new drive block and wedge members being at an angle different from the angle of said first mentioned drive block and wedge members; repeating said spreading of said wedge members and said simultaneous exertion of axial and radial forces to said wedge members; increasing said axial and radial forces until shearing occurs, and registering the values of said axial and radial forces at the time of shearing.

12. A method according to claim 11 and further comprising replacing said drive block and wedge members a plurality of times with drive blocks and wedge members having complementary tapered surfaces, said tapered surfaces being angled differently for each set of drive block and wedge members, repeating the process of claim 6 for each of said different sets of drive blocks and wedge members, whereby different values for the axial and radial forces at the time of shearing will be registered each time the process is repeated.

* * * * *